United States Patent [19]
Shimizu et al.

[11] Patent Number: 5,398,557
[45] Date of Patent: Mar. 21, 1995

[54] ROTARY SAMPLING APPARATUS FOR POWDERED OR GRANULAR MATERIALS

[75] Inventors: Motoharu Shimizu; Osamu Matsui, both of Osaka, Japan

[73] Assignee: Kabushikikaisha Matsui Seisakusho, Osaka, Japan

[21] Appl. No.: 859,004

[22] Filed: Mar. 27, 1992

[51] Int. Cl.⁶ .............................................. G01N 1/20
[52] U.S. Cl. ............... 73/863.52; 73/863.56; 73/863.57; 73/863.81; 73/864.31
[58] Field of Search ........... 73/863.81, 863.51, 863.52, 73/863.53, 863.56, 863.57, 863.83, 863.41, 863.45, 863.82

[56] References Cited

U.S. PATENT DOCUMENTS

| | | | |
|---|---|---|---|
| 3,802,270 | 4/1974 | Daniels et al. | 73/863.52 |
| 4,574,645 | 3/1986 | Allen et al. | 73/863.81 |
| 4,771,642 | 9/1988 | Parth et al. | 73/863.81 |

FOREIGN PATENT DOCUMENTS

| | | | |
|---|---|---|---|
| 905697 | 2/1982 | U.S.S.R. | 73/863.41 |
| 0790960 | 10/1984 | U.S.S.R. | 73/863.41 |

Primary Examiner—Hezron E. Williams
Assistant Examiner—Nashimiya Ashraf
Attorney, Agent, or Firm—Jones, Tullar & Cooper

[57] ABSTRACT

A rotary sampling apparatus for powdered or granular materials wherein the materials are automatically sampled and pneumatically transported to a predetermined place. A first variant of the present invention is of a rod-like type which has a rod-like body having a measuring table. The rod-like type rotary sampling apparatus is designed to be inserted into a bed of powdered or granular materials through an external wall of a storage container such as a hopper dryer. A second variant of the present invention is of a mounted type rotary sampling apparatus with a measuring table and the apparatus is designed to be incorporated into a mounting pedestal provided with the storage container. In both variants of the present invention, the measuring table is rotated by a rotary actuator, a measuring hole of the measuring table is placed at a material sampling position, and powdered or granular materials are sampled and filled in the measuring hole. The hole of the measuring table is rotated into a material discharge position and the materials are forcedly pneumatically discharged through a discharge passage by feeding a pressurized gas.

5 Claims, 11 Drawing Sheets

ROTARY SAMPLING APPARATUS FOR POWDERED OR GRANULAR MATERIALS

BACKGROUND OF THE INVENTION

I. Field of the Invention

The present invention relates to a rotary type sampling apparatus for powdered or granular materials.

The first variant of the present invention relates to a sampling apparatus wherein a rod-like body having a rotary measuring table is designed to be inserted into a bed of powdered or granular materials in a storage container such as a hopper dryer through an external wall of the storage container for powdered or granular materials and a sample of the powdered or granular materials are forcedly pneumatically discharged and automatically taken out by rotating the measuring table and feeding a pressurized gas.

The second variant of the present invention relates to a rotary sampling apparatus which is designed to be incorporated into a mounting pedestal provided for a material storage container and a sample of the powdered or granular materials are forcedly pneumatically discharged and automatically taken out by rotating the measuring table and feeding a pressurized gas.

II. Prior Art

Generally, taking an example of resin materials as powdered or granular materials, it is very important to maintain an appropriate moisture content of the resin materials in view of maintaining good quality of the resin materials because products molded from the resin materials have damages such as a silver line or voids when the moisture content of the resin materials is inappropriate. Therefore, resin materials have always been dried in a hopper dryer for a fixed time before the materials are fed into a moulding machine.

However, it has been difficult to maintain the moisture content of the resin materials constant even if the materials have been dried for a fixed time because the moisture content of resin materials differs depending on the season or other conditions. Therefore, it has proven troublesome to measure the moisture content of resin materials by monitoring drying conditions such as a heating temperature of the hopper dryer which is minutely controlled depending on the measured moisture content.

Manufacturers of resin materials control the quality of the resin materials by repeatedly checking the moisture content thereof when the materials are shipped. However, the checking is all done manually by operator's and this takes a lot of time and labor. Therefore, automation of such checking is desirable but has been considered very difficult.

However, it is necessary to sample resin materials continuously fed at regular intervals for measuring the moisture content of the materials. So, labor saving and automation of such a sampling operation are desired. However, at present, people other than resin manufacturers perform checking of the moisture content of the materials with only a few samplings and only a few times.

Further, the moisture content of resin materials has been generally calculated from the moisture weight contained in the sampled resin materials. In such a case, the weight of the sampled resin materials must not differ in order to calculate an accurate moisture content. Therefore, a high precise quantitative sampling has been desired.

SUMMARY OF THE INVENTION

The present invention was developed in view of the above-mentioned problems. The object of the present invention is to provide a rotary sampling apparatus which can automatically and quantitatively sample powdered or granular materials such as resin materials by accurate means.

The first variant of the present invention which achieves the above-mentioned object is a rotary sampling apparatus which is designed to be inserted into a bed of powdered or granular materials through a side wall of a storage container. The second variant of the present invention which achieves the above-mentioned object is a rotary sampling apparatus which is designed to be incorporated into a mounting pedestal of a storage container.

A rotary sampling apparatus according to the first variant of the present invention comprises a rod-like body with a material sampling port at the side thereof having an introduction passage for a pressurized gas and a discharge passage for powdered or granular materials in the rod-like body. The rod-like body is designed to be secured to an external wall of a storage container for powdered or granular materials by inserting an initial portion of the rod-like body into a bed of powdered or granular materials. A measuring table is rotatably mounted at the tip of the rod-like body and has a material measuring hole for filling the powdered or granular materials sampled through the material sampling port. A scraper is also provided for the rod-like body for scraping off the surplus amount of the powdered or granular materials filled in the measuring hole of the measuring table. A rotary actuator rotates the measuring table so as to change the measuring hole of the measuring table from a material sampling position at a material sampling port side to a material discharge position in which the measuring hole communicates with a connection port of the discharge passage of powdered or granular materials. The rotary sampling apparatus includes pneumatic control means for pneumatically discharging the powdered or granular materials filled in the measuring hole of the measuring table through the material discharge passage by feeding a pressurized gas into the pressurized gas introduction passage in interlocking relation with the rotating action of the rotary actuator.

Figure 3:
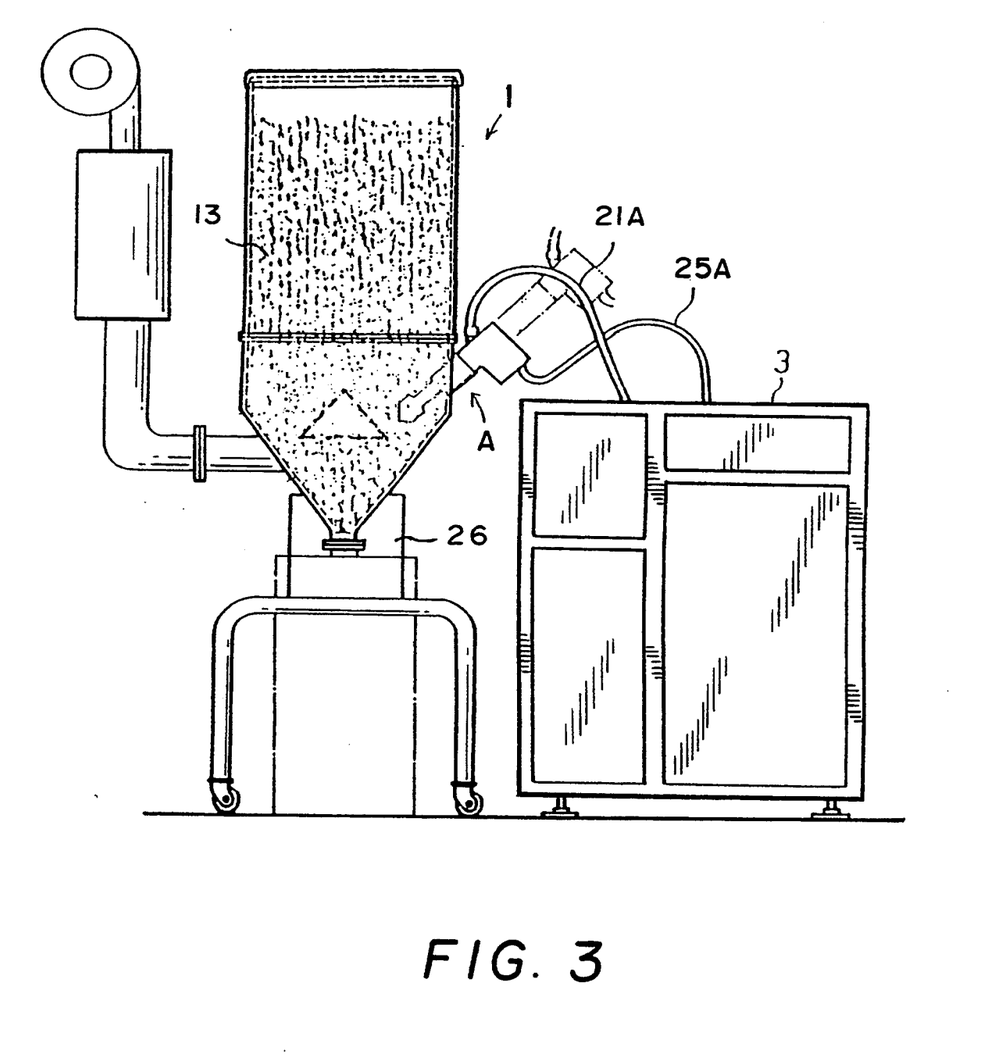
FIG. 3 shows an embodiment wherein a rotary sampling apparatus of the first variant of the present invention is applied to an on-line moisture control system.
Figure 6:
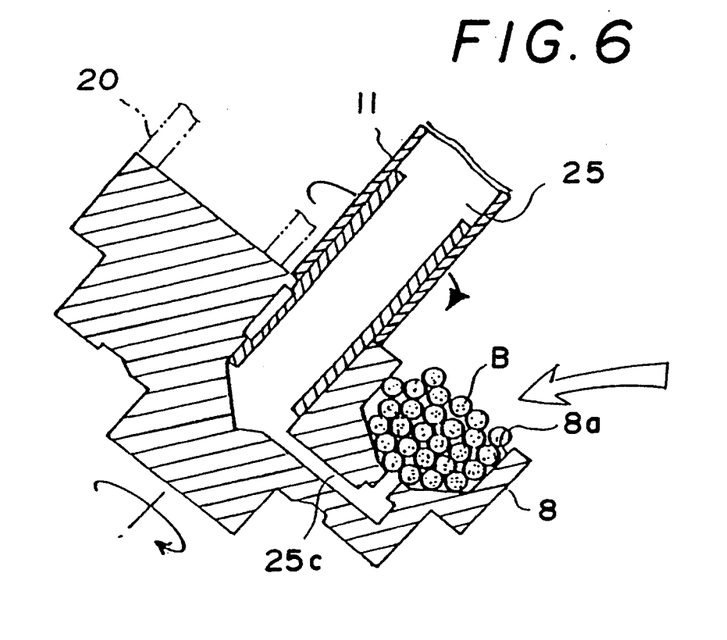
FIG. 6 shows how materials are sampled by the measuring table at a material sampling position.

According to the rotary sampling apparatus of the first variant of the present invention, as shown in FIG. 3, when the rod-like body having the measuring table is inserted into the bed of powdered or granular materials in the storage container, the material sampling port of the body is embedded in the bed of materials. Therefore, powdered or granular materials are filled in the hole of the measuring table through the material sampling port of the rod-like body. (See FIG. 6)

Figure 5:
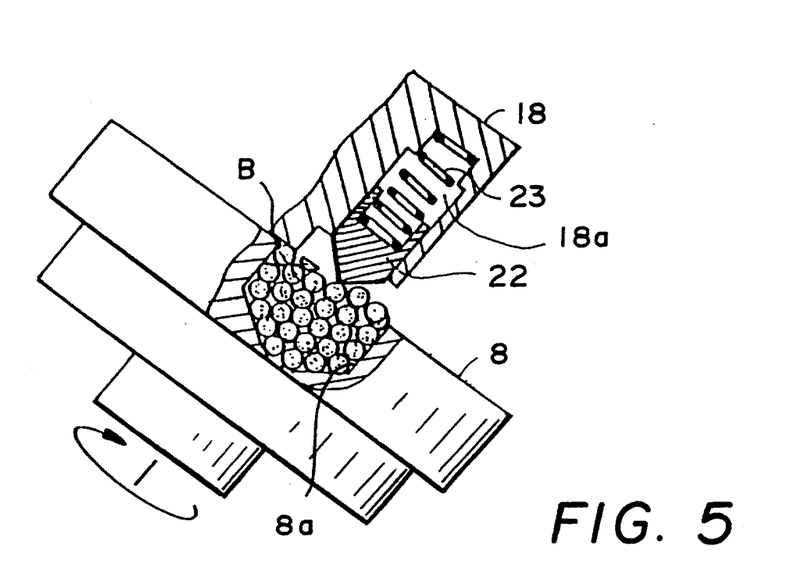
FIG. 5 is a partial vertical sectional view of a measuring table showing a scraper.

Then, the rotary actuator is driven to rotate the measuring hole of the measuring table into the material discharge position. As the scraper scrapes off the surplus amount of the powdered or granular materials piled above the top of the measuring hole when the measuring table 1s rotating (FIG. 5), the powdered or granular materials leveled and filled in the measuring hole can be transferred to the connection port of the material discharge passage.

Figure 7:
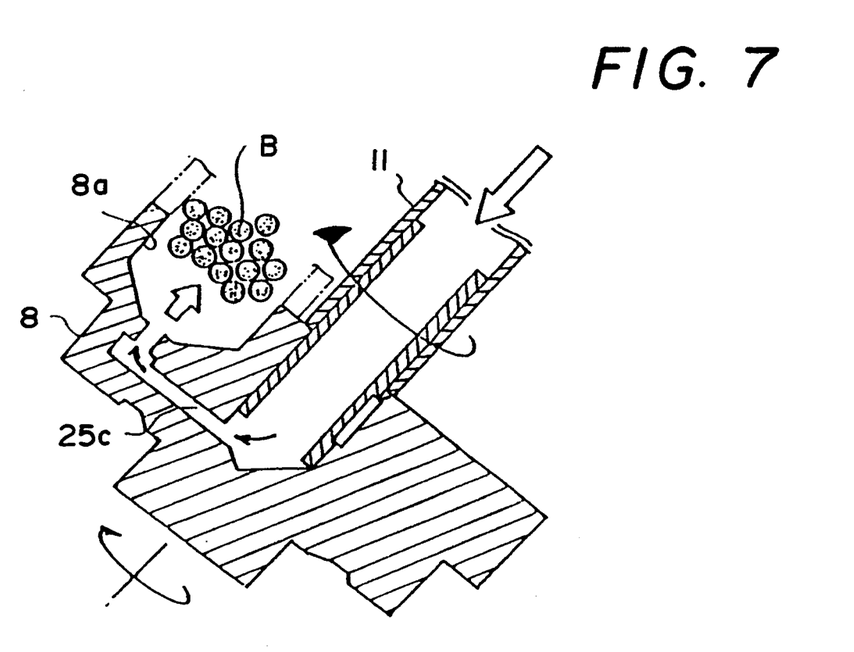
FIG. 7 shows how materials are discharged by a measuring table at a material discharge position.
Figure 8:
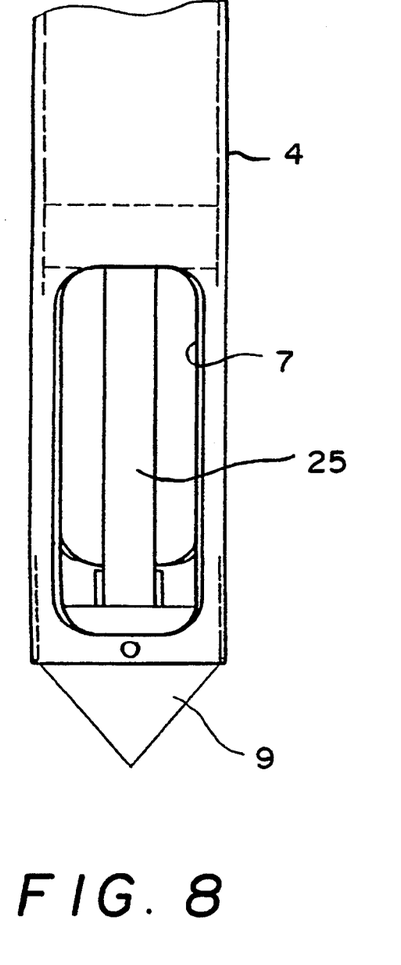
FIG. 8 shows the tip of the rotary sampling apparatus of the first variant of the present invention and illustrates a material sampling port.

When the pneumatic control means is actuated after the measuring hole of the measuring table is moved into the connection port of the material discharge passage, a pressurized gas is fed into the pressurized gas introduction passage and the powdered or granular materials filled in the measuring hole of the measuring table are forcedly pneumatically discharged to the exterior through the material discharge passage by means of the pressurized gas. In such a way, a quantitative sampling is accomplished. (FIG. 7)

A rotary sampling apparatus according to the second variant of the present invention is designed to be incorporated into a mounting pedestal of a storage container for powdered or granular materials such as a hopper dryer, and the mounting pedestal has a vertically penetrating material discharge passage. The rotary sampling apparatus is comprised of a base block having a pressurized gas introduction passage, a sample discharge passage, and a sample storing hole, and the base block is designed to be incorporated into a recess formed in a side wall of the material discharge passage of the mounting pedestal of the material storage container. It is also comprised of a measuring table with a measuring hole and the measuring table is rotatably attached to the base block with a rotating axis inclined so as to face the material discharge passage. Further, it includes a scraper for scraping off surplus amount of the powdered or granular materials filled in the measuring hole of the measuring table, when the scraper is in a position opposite to the measuring table. The sampling apparatus also includes a rotary actuator for rotating the measuring table in order to change the measuring hole of the measuring table from a material sampling position to a sample discharge position in which the measuring hole communicates with the sample storing hole of the base block. The materials filled in the measuring hole fall into the sample storing hole when the measuring hole is rotated to a sample discharge position. Furthermore, the apparatus also includes pneumatic control means for pneumatically discharging the powdered or granular materials stored in the sample storing hole of the base block through the sample discharge passage by feeding a pressurized gas into the pressurized gas introduction passage of the base block which interlocks with the rotation of the rotary actuator.

In such a rotary sampling apparatus, the rotary actuator may be constructed such that it is driven to be rotated by feeding a pressurized gas. And also the rotary actuator may be constructed such that it is driven to be rotated by driving a motor.

Further, the measuring table may be formed with a plurality of measuring holes and the rotary actuator and the pneumatic control means may be interlockingly controlled in order to pneumatically and continuously feed the powdered or granular materials filled in each of the measuring holes of the measuring table.

Furthermore, the measuring table may be of such a detachable type as to allow replacement of various measuring tables with measuring holes different in volume because the sampling amount can be easily changed depending on the volume of the measuring holes of the measuring tables.

Figure 9:
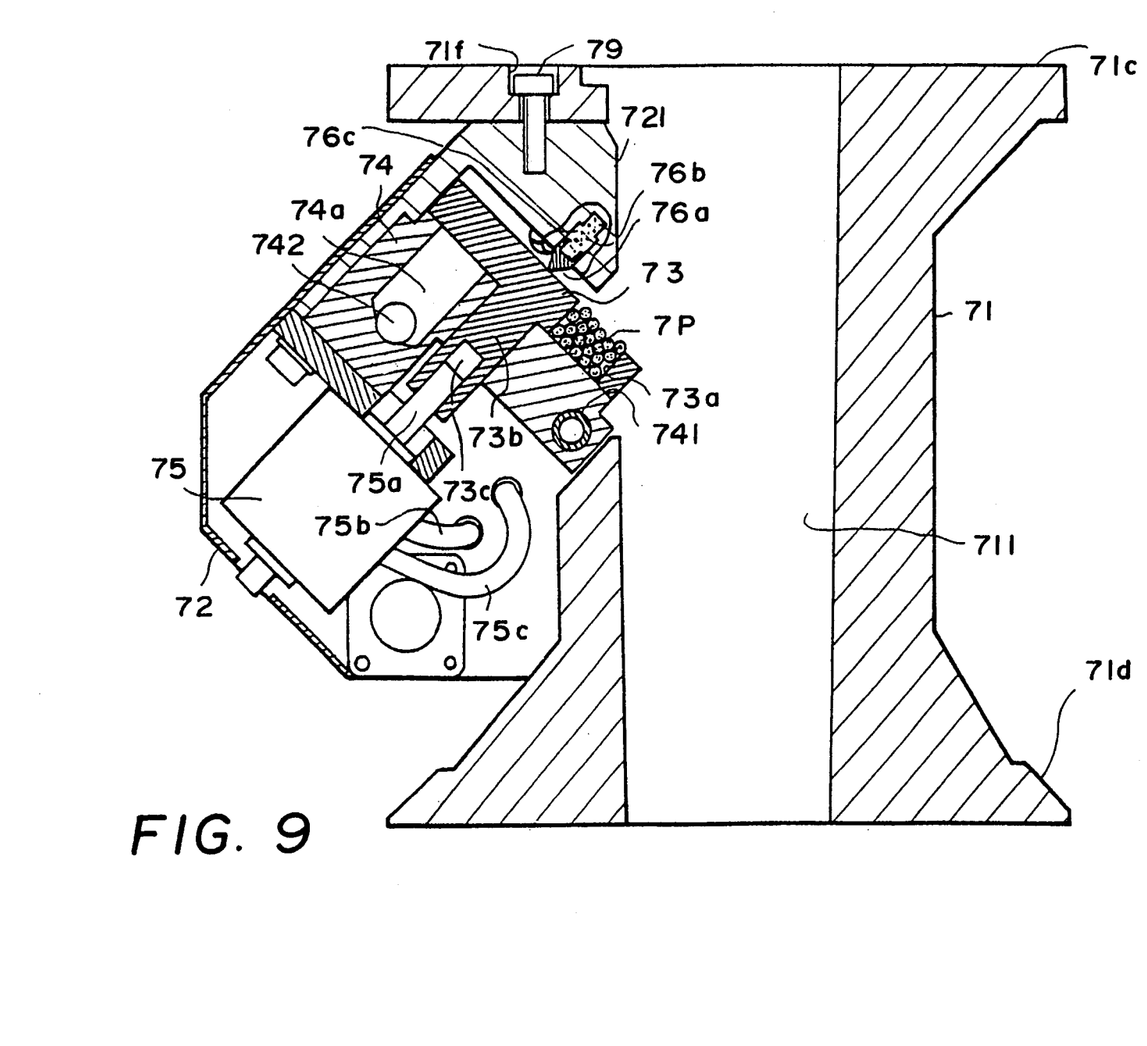
FIG. 9 is a vertical sectional view showing how a rotary sampling apparatus according to the second variant of the present invention is installed. A measuring hole of a measuring table is set to a material sampling position.

According to the rotary sampling apparatus of the second variant of the present invention, as shown in FIG. 9, the powdered or granular materials stored in the material discharge passage can be received in the measuring hole of the measuring table when the measuring hole is in the position facing the material discharge passage vertically penetrating in the mounting pedestal.

Figure 13:
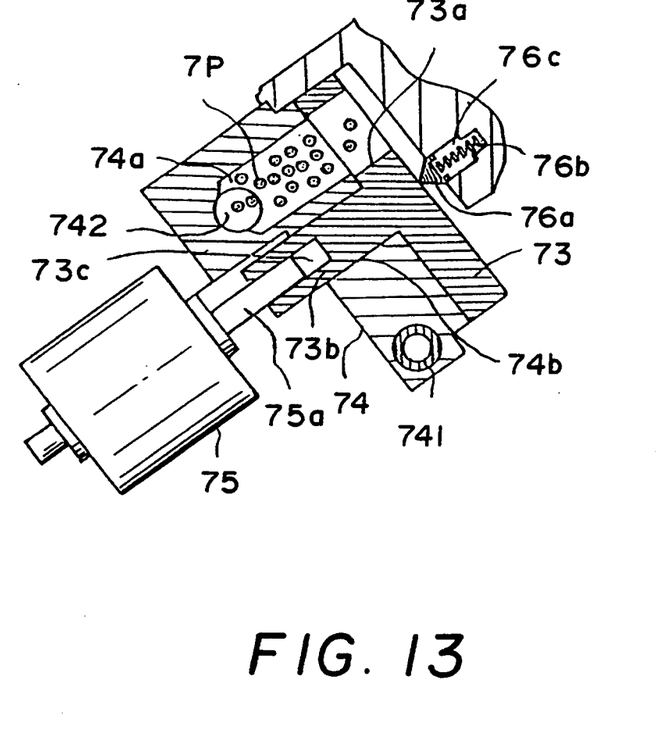
FIG. 13 is a vertical sectional view wherein a measuring hole of a measuring table is set to a sample discharge position.

At this time, the rotary actuator is driven to rotate the measuring hole of the measuring table into the sample discharge position as shown in FIG. 13. Then the measuring hole matches the sample storing hole of the base block and the powdered or granular materials in the measuring hole fall into the sample storing hole to be stored therein. Because the scraper scrapes off the surplus amount of the powdered or granular materials piled at the top of the measuring hole of the measuring table during the rotation, powdered or granular materials leveled and filled in the measuring hole are measured.

After the measuring hole of the measuring table is moved to match the sample storing hole of the base block, a pressurized gas is fed into the pressurized gas introduction passage of the base block by driving the pneumatic control means (not shown). Therefore, the powdered or granular materials stored in the sample storing hole are forcedly pneumatically discharged to the exterior through the sample discharge passage of the base block by the use of the pressurized gas, whereby a quantitative sampling without manpower can be achieved.

DETAILED DESCRIPTION OF A PREFERRED EMBODIMENT

One embodiment of the first variant of the present invention is described hereinafter referring to the attached drawings.

In the embodiment mentioned hereafter, resin materials are used as powdered or granular materials to be stored and dried in a hopper dryer.

Figure 1:
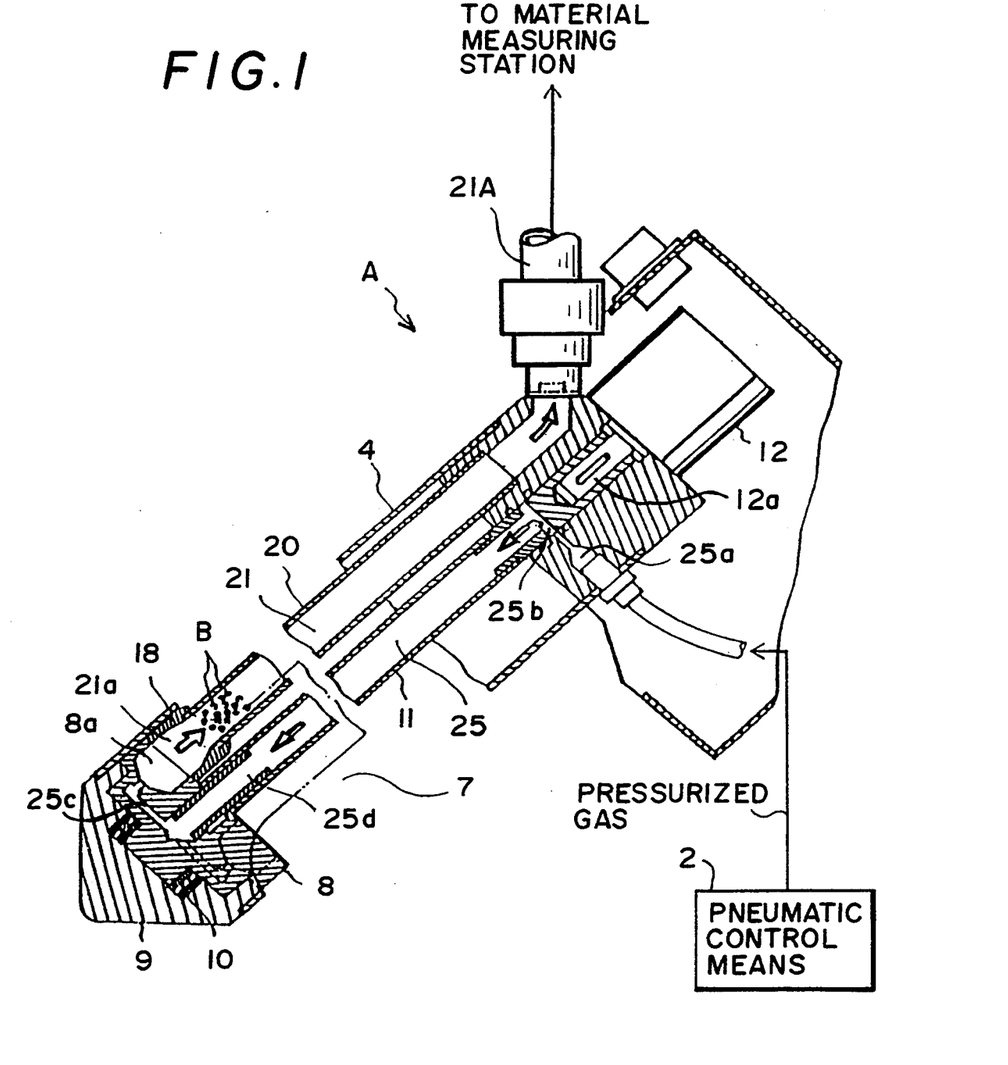
FIG. 1 is a vertical sectional view of one embodiment of a rotary sampling apparatus according to the first variant of the present invention.
Figure 2:
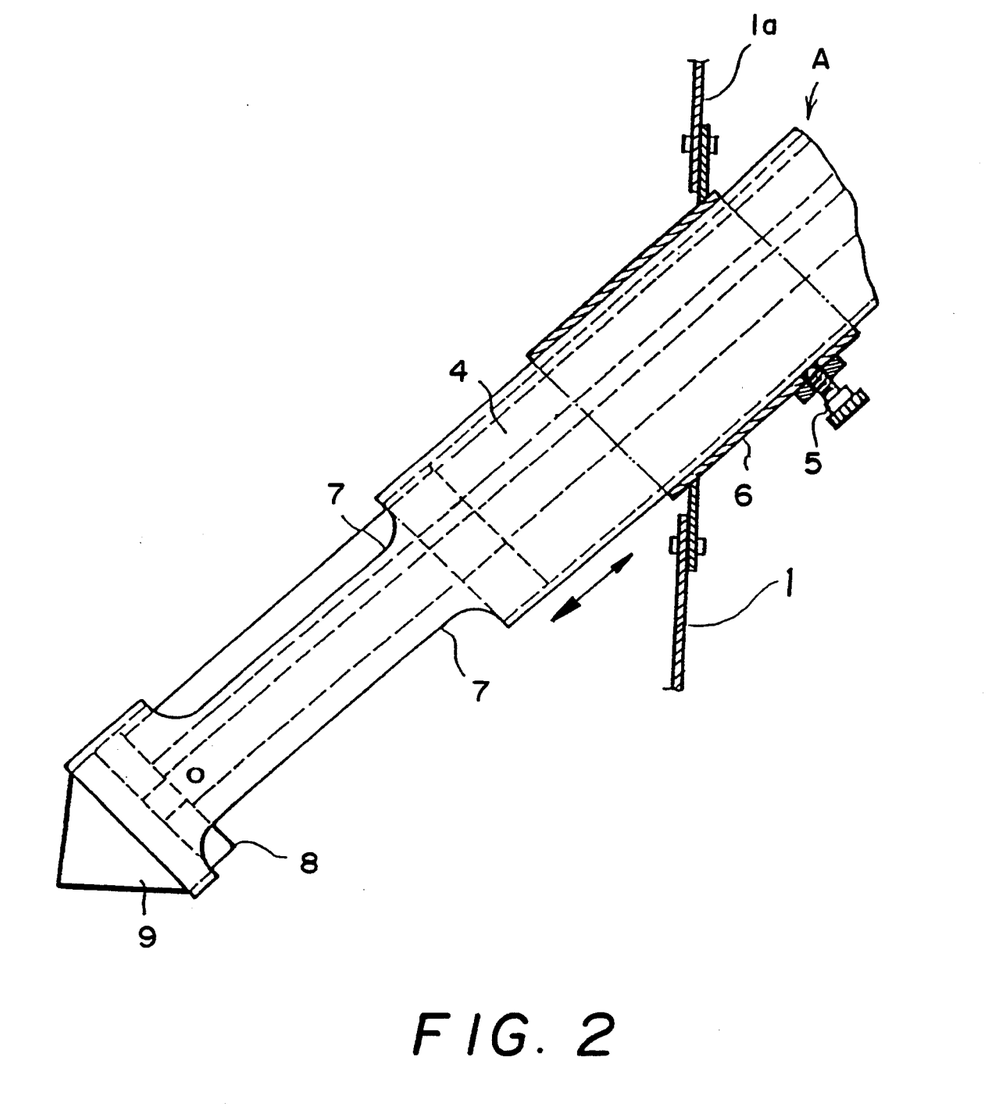
FIG. 2 shows how a rotary sampling apparatus of the first variant of the present invention is attached.

As shown in FIGS. 2 and 3, a sampling apparatus A is comprised of a rod-like body 4 provided with a material sampling port 7 at the side of the initial end thereof and with a cap 9 at the initial end thereof. The cap 9 is formed tapered so as to be easily embedded into a bed of powdered or granular materials 13 in a hopper dryer 1 provided on a resin moulding machine 26. The rod-like body 4 is inserted into a guide cylinder 6 penetrating through a side wall 1a of the hopper dryer 1 and is adjustably slided by means of an adjustment screw 5. (See the arrow in FIG. 2) The material sampling port 7 is inserted into the bed of resin materials 13 in the hopper dryer 1 and embedded therein. An elastic sealing material (not shown) is provided between the rod-like body 4 and the guide cylinder 6 and between the guide cylinder 6 and the side wall 1a of the hopper dryer 1.

In the rod-like body 4, a pressurized gas introduction passage 25 comprised of a hollow pipe 11 of which one end is fixed with a rotary axis 12a of a rotary actuator 12 and a material discharge passage 21 comprised of a hollow pipe 20 are provided parallel and in a longitudinal direction. The other end of the pressurized gas introduction passage 25 communicates with a measuring hole 8a of a measuring table 8 through a connecting short pipe 25d projecting out of the center of the measuring table 8. A connecting port 21a of the material discharge passage 21 communicates with the measuring hole 8a of the measuring table 8 when the measuring hole 8a rotates into a material discharge position, as shown in FIG. 7. The pressurized gas introduction passage 25 and the material discharge passage 21 communicate through a communicating passage 25c. A connecting port 25a of the pressurized gas introduction passage 25 is connected with pneumatic control means 2 including a compressor or the like through a flexible hose 25A to supply dried nitrogen gas or dried air when the pneumatic control means is actuated. The material discharge passage 21 is connected to a moisture measuring station 3, described hereinafter, through a flexible hose 21A.

The measuring table 8 having the measuring hole 8a is rotatably supported by a bearing 10 in the cap 9 provided at the initial end of the rod-like body 4. Therefore, the measuring hole 8a can be switched from the material sampling position shown in FIG. 6 to the material discharge position shown in FIG. 7 when a rotating axis 12a of the rotary actuator 12 rotates. In this embodiment the rotary actuator 12 rotates by driving the rotating axis 12a by means of a pressurized gas fed form the pneumatic control means 2. However, the rotary actuator 12 may be constructed such that it is driven to be rotated by means of a solenoid or a motor. The measuring table 8 can be rotated at a low speed when a motor is used, whereby the sampled resin materials B aren't damaged when the cap 9 of the rod-like body 4 is embedded in the bed of resin materials 13.

Figure 4:
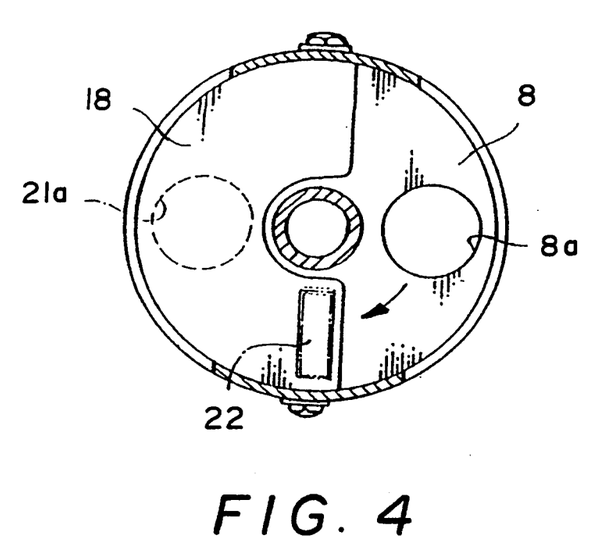
FIG. 4 is a plane view of a measuring table.

FIG. 4 is a plane view of the measuring table 8. A scraper 22 is provided at the rod-like body side of the measuring table 8. The scraper 22 scrapes off the surplus amount of the resin materials B filled in the measuring hole 8a when the measuring table 8 is rotated. The scraper 22 is tapered and is elastically supported by a spring 23 contained in a recess 18a of a half-round fixing board 18 provided for the rod-like body 4. Therefore, the scraper 22 can scrape extra resin materials B piled in the measuring hole 8a without damaging the materials when the measuring table 8 is rotated.

FIG. 3 is an overall view of an on-line moisture control system of pelletized resin materials employing the sampling apparatus A of the first variant of the present invention. In this embodiment, the sampling apparatus A is attached to the side wall 1a of the hopper dryer 1 storing pelletized resin materials as shown in FIG. 2 and the cap 9 provided with the material sampling port 7 is embedded in the bed of resin materials 13 in the hopper dryer 1.

The pressurized gas introduction passage 25 is connected to the pneumatic control means (not shown) provided in a moisture measuring unit comprising the moisture measuring station 3 through the flexible hose 25A and the material discharge passage 21 is connected to the moisture measuring device (not shown) in the moisture measuring unit through the flexible hose 21A. The moisture measuring unit includes the moisture measuring device wherein the sampled resin materials B are heated and the moisture content of the materials B is calculated by means of a color comparing measuring method using a Karl Fischer reagent. When the resin materials B are sampled by means of the sampling apparatus A, the moisture content of the sampled materials can be automatically measured by the moisture measuring device.

According to this moisture control system, the moisture content of the resin materials B sampled as mentioned above is measured sequentially. The heater temperature and wind flow amount in the hopper dryer are automatically controlled according to the measured moisture content, whereby the moisture content of the resin materials B can be optionally controlled. In such a system, the moisture content of the resin materials B can be controlled by an on-line system wherein the moisture of the resin materials B sampled at random without using manpower is measured and a constant moisture content is kept according to the measured value.

Operation of the sampling apparatus A of the first variant of the present invention is described hereinafter.

The rod-like body 4 is attached to the side wall 1a of the hopper dryer 1 by means of the guide cylinder 6 so that the material sampling port 7 at the initial end of the rod-like body 4 is fully embedded in the bed of resin materials 13 in the hopper dryer 1.

In order to sample the resin materials B out of the bed of the resin materials 13, the rotary actuator 12 is driven and the measuring table 8 is rotated so that the measuring hole 8a moves from the material sampling position to the material discharge position. Then, the measuring hole 8a filled with the resin materials B through the material sampling port 7 when the measuring hole 8a is positioned at the material sampling position is joined with the connecting port 21a of the material discharge passage 21 after extra resin materials piled on the measuring hole 8a is scraped by the scraper 22. At this time, a pressurized gas is fed into the pressurized gas introduction passage 25 by actuating the pneumatic control means 2. The pressurized gas enters the measuring hole 8a of the measuring table 8 through the communicating passage 25c and forcedly pneumatically transfer the resin materials B in the measuring hole 8a into the moisture measuring station 3 through the material discharge passage 21.

After the resin materials B filled in the measuring hole 8a are pneumatically transported into the moisture measuring station 3, the measuring hole 8a is returned to the material sampling position by rotating the rotary actuator 12. Resin materials are filled in the measuring hole 8a of the measuring table 8, discharged by means of the pneumatic control means 2 into the material discharge passage 21, and pneumatically transported into the moisture measuring station 3 in the same way mentioned above.

The above-mentioned procedure is repeated and resin materials are continuously automatically sampled out of the hopper dryer without manpower.

The concrete construction of the first variant of the present invention isn't limited to the above-mentioned embodiments. For example, a plurality of measuring holes 8a may be provided for the measuring table 8. In such a case, a pressurized gas may be fed by the pneumatic control means 2 each time one of the measuring holes 8a is rotated from the material sampling position to the material discharge position, whereby the resin materials filled in the measuring holes 8a can be sampled sequentially.

Further, a plurality of measuring tables having measuring holes of different volume may be prepared and removably attached to the initial portion of the rod-like body 4.

According to the sampling apparatus A of the first variant of the present invention, the rod-like body 4 is inserted into the bed of powdered or granular materials 13 and the rotation of the rotary actuator 12 and the feeding of a pressurized gas of the pneumatic control means 2 are controlled. By repeating such operations, powdered or granular materials are quantitatively sampled without using manpower.

Therefore, when this apparatus is applied to the moisture measuring of resin materials, automation of sampling operation is achieved and consequently labor saving is also achieved. In addition, this apparatus can attribute to the improvement of the moisture control system because this sampling apparatus is good at quantitativity and can perform a highly accurate moisture measuring.

Further, if this apparatus is applied to a material storing tank just before shipping, moisture control at the time of shipment can be automatically done. Therefore, the materials can be shipped while maintaining good quality.

One embodiment according to the second variant of the present invention is described hereinafter referring to the attached drawings.

In the embodiment resin materials are used as powdered or granular materials to be stored and dried in a hopper dryer.

Figure 10:
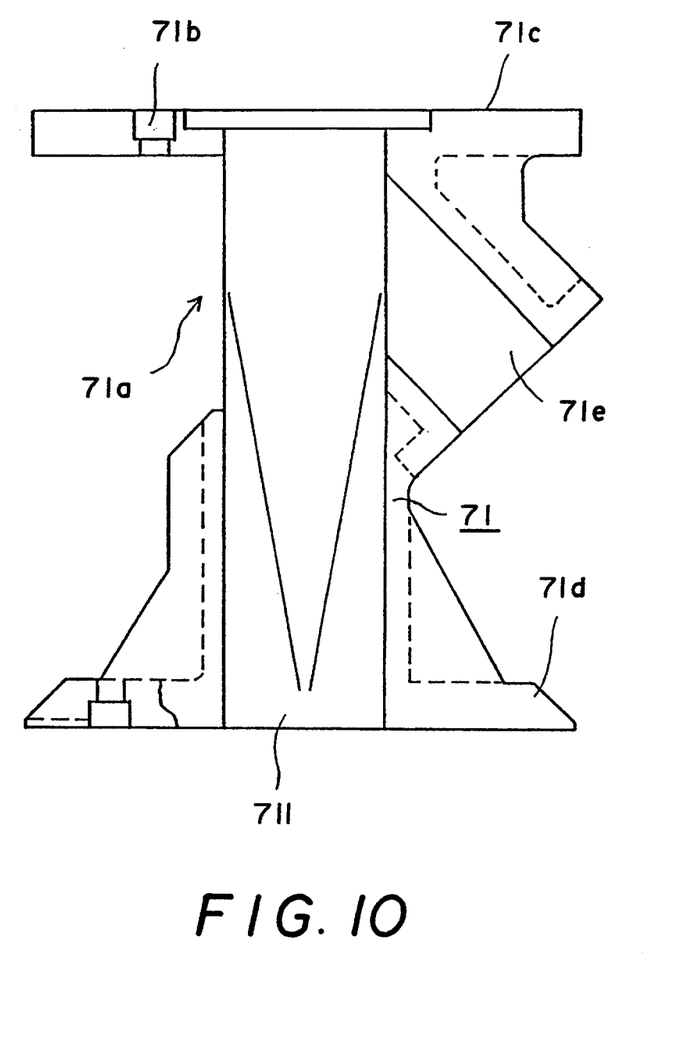
FIG. 10 is a vertical sectional view of a mounting pedestal to which a rotary sampling apparatus of the second variant of the present invention is attached.
Figure 14:
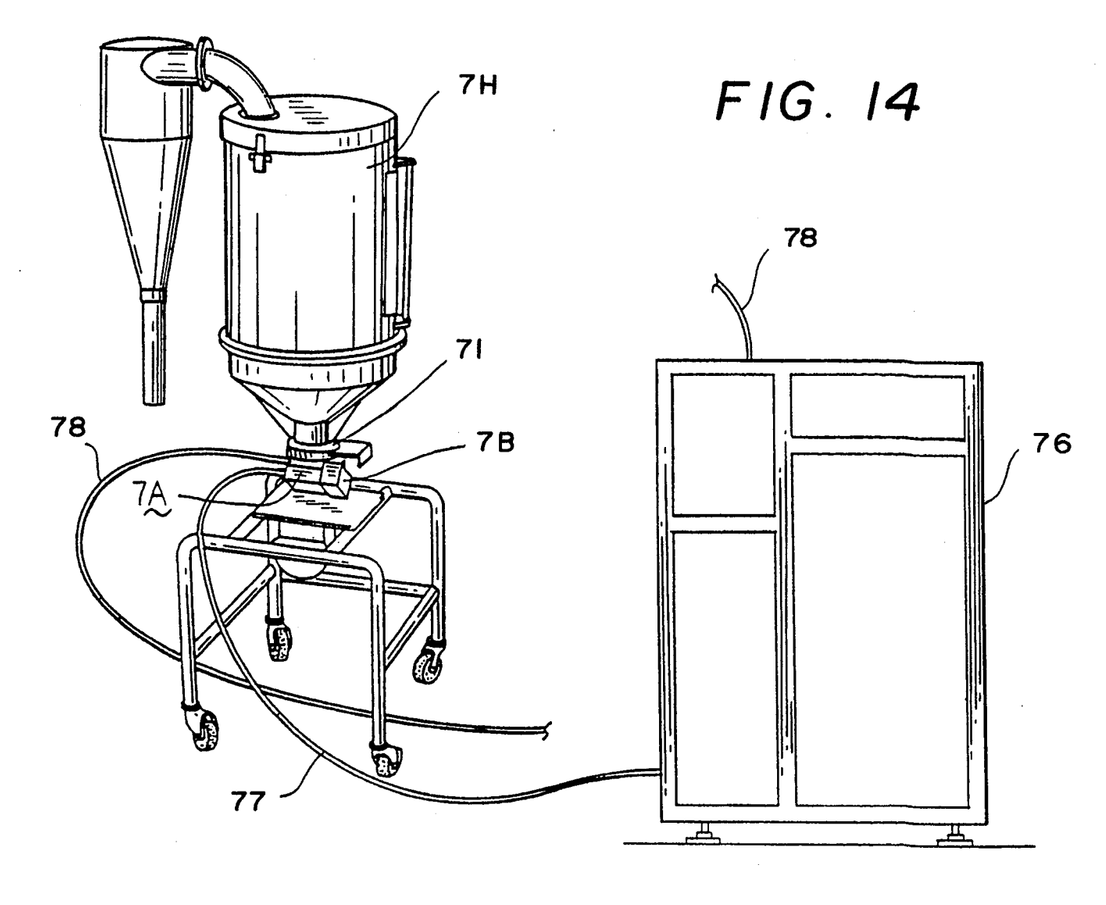
FIG. 14 is a view showing an embodiment to which a rotary sampling apparatus of the second variant of the present invention is applied.

A mounting pedestal 71 to which a rotary sampling apparatus 7A of the second variant of the present invention is incorporated is provided with guards 71c and 71d at the top and bottom thereof, a recess 71a at one side wall, and a material discharge port 71e at the other side wall as shown in FIG. 10. A hopper dryer 7H can be fixed to the upper guard 71c of the pedestal 71 by fixing means such as a bolt (not shown) as shown in FIG. 14. And the mounting pedestal 71 has a material discharge passage 711 vertically penetrating in the center thereof.

The rotary sampling apparatus 7A is designed to be incorporated in the recess 71a formed by cutting out one side wall of the material discharge passage 711 vertically penetrating in the mounting pedestal 71 to which the hopper dryer 7H is attached as shown in FIG. 14. A fitting part 721 of a housing 72 is attached with the upper guard 71c of the mounting pedestal 71 by screwing a bolt 79 into a hole 71f.

Figure 11:
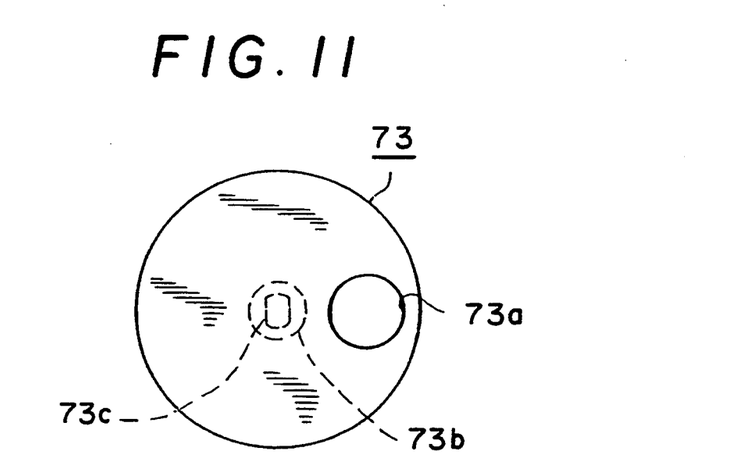
FIG. 11 shows one embodiment of a measuring table according to the second variant of the present invention.

A half-round measuring table 73 with a measuring hole 73a having a diameter matching to that of a sample storing hole 74a of a base block 74 is included in the housing 72. (A plane view of the measuring table 73 is shown in FIG. 11) As shown in FIG. 9, the measuring table is rotatably and inclinedly disposed in the recess 71a a so as to face the material discharge passage 711, in order to take some of the powdered or granular materials charged in the discharge passage as samples. A rotating axle 73b of the measuring table 73 penetrates into an axial hole 74b formed at the center of the base block 74 and a rotating axis 75a of a rotary actuator 75 is inserted into a recess 73c provided at the tip of the rotating axle 73b and connected with each other.

Figure 12:
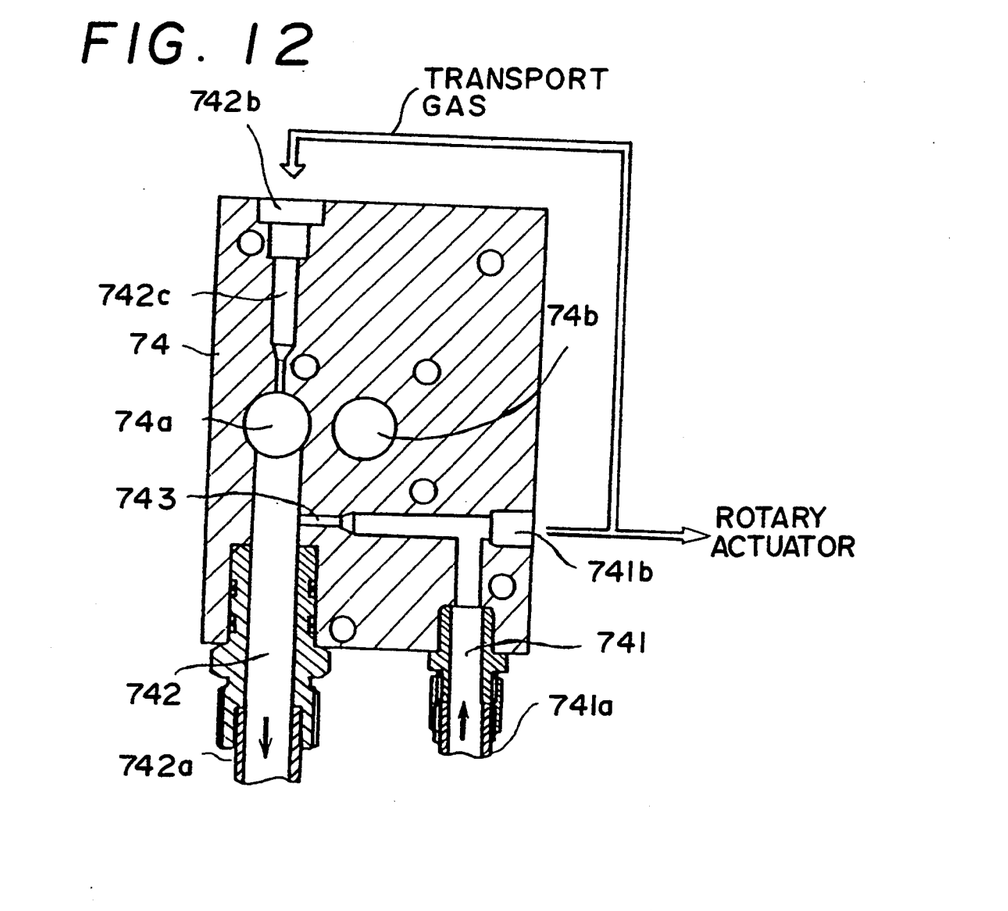
FIG. 12 is a fragmentary sectional view of a base block.

The base block 74 includes a pressurized gas introduction passage 741 having a gas introduction port 741a for introducing a pressurized gas and also includes a sample discharge passage 742 having the sample storing hole 74a. The base block 74 is designed to be incorporated into the recess 71a formed in a side wall of the material discharge passage in such a manner that the block 74 is contained in the recess 71a. The pressurized gas introduced into the pressurized gas introduction passage 741 is fed as a driving gas from a gas discharge port 741b thereof into an air cylinder constructed as a driving part of the rotary actuator 75. And the pressurized gas is also fed as a transport gas for transporting a sample of powdered or granular materials into the sample discharge passage 742 through a connecting port 742b and a connecting portion 742c.

The sample storing hole 74a is provided in the sample discharge passage 742 formed in the base block 74 and a communicating passage for purging 743 bypassed by a thin communicating pipe from the gas introduction port 741a is provided at the downstream of the hole 74a.

The communicating passage 743 is provided so as to forcibly discharge water in pipings, the water of which has a bad effects on samples, before materials are sampled by feeding a pressurized gas From the gas introduction port 741a.

The introduction port 741a of the pressurized gas introduction passage 741 is connected to pneumatic control means comprised of a compressor by means of a flexible hose 77. When the pneumatic control means is actuated, dried nitrogen gas or dried air is fed into the introduction port 741a. The gas discharge port 742a of the sample discharge passage 742 is connected to a moisture measuring station 76, described hereinafter, through a flexible hose 78.

The measuring hole 73a of the measuring table 73 is switched from a material sampling position as shown in FIG. 9 to a sample discharge position as shown in FIG. 13 when the rotating axle 75a of the rotary actuator 75 rotates.

In this embodiment, the rotating axle 75a of the rotary actuator 75 is driven to be rotated by means of a pressurized gas fed from the pneumatic control means housed in the moisture measuring station 76. However, it may be constructed such that it is driven to be rotated by means of a solenoid or a motor. The measuring table 73 can be rotated at a low speed when a motor is used, whereby the materials 7P sampled from the material discharge passage 711 penetrating vertically through the mounting pedestal 71 aren't damaged.

A scraper 76a scrapes extra resin materials filled in the measuring hole 73a when the measuring table 73 is rotated and the scraper 76a is provided at the portion corresponding to the upper part of the measuring table 73 in the recess 71a formed at one side wall of the material discharge passage 711. The scraper 76a having a tapered tip is provided in the recess 71a so as to come in contact with the face of the measuring table 73 and is elastically supported by a spring 76b housed in a hole 76c formed at the upper part of the recess 71a as shown in FIGS. 9 and 13. Therefore, extra resin materials 7P piled in the measuring hole 73a can be scraped off without being damaged when the measuring table 73 is rotated from the material sampling position to the sample discharge position.

FIG. 14 is an overall view of an on-line moisture control system for resin materials employing the sampling apparatus 7A of the second variant of the present invention. In this embodiment, the sampling apparatus 7A and a solenoid valve 7B for controlling the rotary actuator 75 are attached in a pair to the mounting pedestal 71 of the hopper dryer 7H storing pelletized resin materials.

The pressurized gas introduction passage 741 and the sample discharge passage 742 of the base block 74 of the sampling apparatus 7A are connected to the pneumatic control means (not shown) through the flexible hose 77 and the moisture measuring device (not shown) through the flexible hose 78 respectively, and the pneumatic control means and the moisture measuring device are provided in the moisture measuring unit constructing the moisture measuring station 76.

The moisture measuring station 76 houses the moisture measuring device wherein the sampled resin materials 7P are heated and the moisture content of the materials 7P is calculated by means of a color comparing measuring method using a Karl Fischer reagent. When the resin materials 7P are sampled by means of the sampling apparatus 7A, the moisture content of the sampled materials can be automatically measured by the moisture measuring device.

According to this moisture control system, the moisture content of the resin materials 7P sampled as mentioned above is measured sequentially. The heater temperature and wind flow amount in the hopper dryer are automatically controlled according to the measured moisture content, whereby the moisture content of the resin materials can be optionally controlled. In such a system, the moisture content of the resin materials 7P can be controlled by an on-line system wherein the moisture of the resin materials 7P sampled at random without using manpower is measured and a constant moisture content is kept according to the measured value.

Operations of the sampling apparatus 7A of the second variant of the present invention is described hereinafter.

The housing 72 is attached to the mounting pedestal 71 of the hopper dryer 7H by means of the bolt 79. The bolt 79 is adjustably bolted so that the measuring hole 73a of the measuring table 73 meets the material sampling position facing the material discharge passage 711 and the sample discharge position by controlling rotation of the rotary actuator 75.

After the housing 72 is attached to the mounting pedestal 71 of the hopper dryer 7H, for sampling resin materials 7P, the rotary actuator 75 is driven to be rotated by actuating the solenoid valve 7B so that the measuring hole 73a of the measuring table 73 moves from the material sampling position to the sample discharge position.

Then, the resin materials 7P filled in the measuring hole 73a from the material discharge passage 711 when the measuring hole 73a is located at the material sampling position are scraped their surplus amount by the scraper, the materials 7P fall into the sample storing hole 74a of the base block 74 from the measuring hole 73a, and they are contained therein. At this time, a pressurized gas is fed into the pressurized gas introduction passage 741a of the base block 74 by actuating the pneumatic control means and the resin materials 7P stored in the sample storing hole 74a are forcedly pneumatically discharged from the sample discharge port 742b together with the pressurized gas and pneumatically transported into the moisture measuring station 76 through the flexible hose 78.

After the resin materials 7P filled in the measuring hole 73a are pneumatically transported into the moisture measuring station 76 as described above, the measuring hole 73a is returned to the material sampling position by driving the rotary actuator 75 and filled with the resin materials 7P. The rotary actuator 75 is rotated and the resin materials 7P filled in the measuring hole 73a are contained in the sample storing hole 74a of the base block 74. Then a pressurized gas is fed by driving the pneumatic control means and the sampled resin materials 7P can be pneumatically transported into the moisture measuring station 76.

Feeding of a pressurized gas by the pneumatic control means and rotating of the rotary actuator 75 are repeatedly performed as mentioned above, whereby pelletized resin materials in the hopper dryer can be continuously automatically sampled without manpower.

The concrete construction of the present invention isn't limited to the above-mentioned embodiments. For example, a plurality of measuring holes 73a may be formed with the measuring table 73. In such a case, a pressurized gas may be fed by the pneumatic control means each time one of the measuring holes 73a is rotated from the material sampling position to the material discharge position, whereby the resin materials filled in the measuring holes 73a can be sampled sequentially.

Further, various measuring tables of detachable type with measuring holes of different volume may be used.

According to the sampling apparatus 7A of the second variant of the present invention, the housing 72 is constructed so as to be attached to the mounting pedestal 71 of the hopper dryer 7H, whereby a troublesome exchanging operation isn't required when the hopper dryer 7H to be fixed on the mounting pedestal 71 is exchanged.

Rotation control of the rotary actuator 75 and feeding control of a pressurized gas by the pneumatic control means are repeatedly performed, and resin materials can be quantitatively sampled by pneumatic transportation without manpower. Therefore, when this apparatus is applied to the measuring of the moisture content of the resin materials, automation of sampling operation is achieved and consequently labor saving is also achieved. In addition, this apparatus attributes to the improvement of the moisture control system because this sampling apparatus is good at quantitativity and performs highly accurate moisture measuring.

What is claimed is:

1. A rotary sampling apparatus for powdered or granular materials designed to be incorporated into a mounting pedestal of a material storage container, said mounting pedestal having a material discharge passage extending therethrough, said apparatus comprising:

a base block having a pressurized gas introduction passage, a sample discharge passage, and a sample storing hole, said base block being adapted to be incorporated into a recess formed in a side wall of said pedestal and in communication with said material discharge passage in such a manner that said block is contained in said recess;

a rotatable measuring table with a measuring hole, said measuring table being inclined in said recess relative to said material discharge passage so as to face said material discharge passage in order to receive a portion of the powdered or granular materials charged in said material discharge passage as samples, said portion received including a surplus amount;

a scraper for scraping off said surplus amount of the powdered or granular materials received in said measuring hole of said measuring table, said scraper being provided in said recess so as to contact said measuring table;

a rotary actuator for rotating said measuring table in order to change said measuring hole of said measuring table from a material sampling position to a sample discharge position in which said measuring hole matches said sample storing hole of said base block; and pneumatic control means for forcedly and pneumatically discharging the powdered or granular materials received in said measuring hole of said measuring table less said surplus amount through said sample discharge passage after having dropped the materials received in said measuring hole of said measuring table into said sample storing hole of said base block by feeding a pressurized gas into said pressurized gas introduction passage of said base block.

2. A rotary sampling apparatus as set forth in claim 1, wherein said rotary actuator is constructed such that it is driven to be rotated by feeding a pressurized gas.

3. A rotary sampling apparatus as set forth in claim 1, wherein said rotary actuator is constructed such that it is driven to be rotated by driving a motor.

4. A rotary sampling apparatus as set forth in claims 1, 2 or 3 wherein said measuring table is provided with a plurality of measuring holes, and wherein said pneumatic control means controls feeding of the pressurized gas, whereby the powdered or granular materials received in said plurality of measuring holes formed in said measuring table are sequentially and pneumatically discharged through said material discharge passage.

5. A rotary sampling apparatus for powdered or granular materials as set forth in claims 1, 2, or 3 wherein said measuring table is detachable so as to allow replacement with one of various measuring tables with measuring holes different in volume.

* * * * *